USOO5562650A

United States Patent [19]
Everett et al.

[11] Patent Number: 5,562,650
[45] Date of Patent: Oct. 8, 1996

[54] ABSORBENT ARTICLE HAVING AN IMPROVED SURGE MANAGEMENT

[75] Inventors: Rob D. Everett, Menasha, Wis.; David F. Bishop, Dunwoody; Clifford J. Ellis, Woodstock, both of Ga.; Mark G. Heath, Butte des Morts; Daniel R. Laux, Appleton, both of Wis.; Maria E. Signoret, Greenville, Wis.

[73] Assignee: Kimberly-Clark Corporation, Neenah, Wis.

[21] Appl. No.: 206,816

[22] Filed: Mar. 4, 1994

[51] Int. Cl.$^6$ .................................................. A61F 13/15
[52] U.S. Cl. ........................ 604/378; 607/358; 607/385.1; 607/385.2
[58] Field of Search ..................... 604/358, 378, 604/385.1, 385.2

[56] References Cited

U.S. PATENT DOCUMENTS

| | | | |
|---|---|---|---|
| 2,046,763 | 7/1936 | Asnes | 91/68 |
| 2,570,011 | 10/1951 | Stamberger | 128/287 |
| 2,737,179 | 3/1956 | Dahle | 128/156 |
| 3,113,570 | 12/1963 | Holliday et al. | 128/284 |
| 3,122,142 | 2/1964 | Crowe, Jr. | 128/296 |
| 3,123,075 | 3/1964 | Stamberger | 128/287 |
| 3,221,738 | 12/1965 | Ekberg et al. | 128/287 |
| 3,431,911 | 3/1969 | Meisel, Jr. | 128/287 |
| 3,559,649 | 2/1971 | Grad et al. | 128/290 |
| 3,572,342 | 3/1971 | Lindquist et al. | 128/287 |
| 3,612,055 | 10/1971 | Mesek et al. | 128/287 |
| 3,683,916 | 8/1972 | Mesek et al. | 128/287 |

(List continued on next page.)

FOREIGN PATENT DOCUMENTS

| | | |
|---|---|---|
| 884608 | 11/1971 | Canada . |
| 984280 | 2/1976 | Canada . |
| 1033903 | 7/1978 | Canada . |
| 1314696 | 3/1993 | Canada . |
| 0165807 | 12/1985 | European Pat. Off. ........ A61F 13/16 |
| 0339461 | 11/1989 | European Pat. Off. . |
| 0391476 | 10/1990 | European Pat. Off. ........ A61F 13/15 |
| 0397110A2 | 11/1990 | European Pat. Off. . |
| 0432882 | 6/1991 | European Pat. Off. ........ A61F 13/15 |
| 0483592A1 | 5/1992 | European Pat. Off. . |
| 0523683 | 1/1993 | European Pat. Off. ........ A61F 13/46 |
| 0532002A1 | 3/1993 | European Pat. Off. . |
| 0536941A3 | 4/1993 | European Pat. Off. . |
| 0539703A1 | 5/1993 | European Pat. Off. . |
| 0525778A3 | 2/1994 | European Pat. Off. . |

(List continued on next page.)

*Primary Examiner*—John G. Weiss
*Assistant Examiner*—Dennis Ruhl
*Attorney, Agent, or Firm*—Paul Yee

[57] ABSTRACT

Generally stated, the present invention provides a distinctive absorbent article which includes a backsheet layer and an absorbent retention portion which is superposed on the backsheet layer. The retention portion has a length and a width, and has laterally opposed side edges thereof and longitudinally opposed end edges thereof. A surge management portion is located adjacent a bodyside surface of the retention portion. The surge management portion is constructed to temporarily hold received liquid and release the liquid to the retention portion. The surge management portion has a width, opposed side edges thereof and opposed end edges thereof, and has a length thereof which is less than the length of the retention portion. The end edges of the surge management portion are located longitudinally inboard from the end edges of the retention portion. A porous topsheet layer is disposed in facing relation with the backsheet layer to sandwich the retention portion and the surge management portion between the backsheet layer and the topsheet layer. The topsheet layer has marginal regions thereof attached to marginal regions of the backsheet layer. The attached marginal regions of the topsheet and backsheet layers are located laterally outboard of the side edge regions of the surge management portion. A surfactant material is applied to a medial section of the topsheet layer to provide a greater wettability of the medial section, as compared to a remainder of the topsheet layer. The medial section has a width which is substantially not more than the width of the surge management portion.

23 Claims, 4 Drawing Sheets

U.S. PATENT DOCUMENTS

| | | | |
|---|---|---|---|
| 3,693,622 | 9/1972 | Jones, Sr. | 604/381 |
| 3,730,184 | 5/1973 | Mesek | 128/287 |
| 3,779,246 | 12/1973 | Mesek et al. | 128/287 |
| 3,799,167 | 3/1974 | Miler et al. | 128/287 |
| 3,814,101 | 6/1974 | Kozak | 128/287 |
| 3,825,006 | 7/1974 | Ralph | 128/287 |
| 3,837,343 | 9/1974 | Mesek | 128/287 |
| 3,838,692 | 10/1974 | Levesque | 128/284 |
| 3,848,598 | 11/1974 | Mesek | 128/287 |
| 3,916,900 | 11/1975 | Breyer et al. | 604/378 |
| 3,934,588 | 1/1976 | Mesek et al. | 128/290 W |
| 3,967,623 | 7/1976 | Butterworth et al. | 128/287 |
| 3,987,792 | 10/1976 | Hernandez et al. | 128/284 |
| 4,015,604 | 4/1977 | Csillag | 238/287 |
| 4,044,768 | 8/1977 | Mesek et al. | 128/287 |
| 4,073,852 | 2/1978 | Mesek | 264/122 |
| 4,077,410 | 3/1978 | Butterworth et al. | 128/287 |
| 4,240,416 | 12/1980 | Boich | 128/156 |
| 4,286,082 | 8/1981 | Tsubakimoto et al. | 526/240 |
| 4,585,448 | 4/1986 | Enloe | 604/378 |
| 4,585,449 | 4/1986 | Karami | 604/378 |
| 4,673,402 | 6/1987 | Weisman et al. | 604/368 |
| 4,699,619 | 10/1987 | Bernardin | 604/378 |
| 4,699,823 | 10/1987 | Kellenberger et al. | 428/219 |
| 4,704,116 | 11/1987 | Enloe | 604/385 A |
| 4,738,677 | 4/1988 | Foreman | 604/378 |
| 4,755,179 | 7/1988 | Shiba et al. | 604/370 |
| 4,778,459 | 10/1988 | Fuisz | 604/378 |
| 4,798,603 | 1/1989 | Meyer et al. | 604/378 |
| 4,804,378 | 1/1989 | Shiba et al. | 604/367 |
| 4,820,294 | 4/1989 | Morris | 604/383 |
| 4,834,735 | 5/1989 | Alemany et al. | 604/368 |
| 4,886,512 | 12/1989 | Damico et al. | 609/385.2 |
| 4,888,231 | 12/1989 | Angstadt | 427/213 |
| 4,892,528 | 1/1990 | Suzuki et al. | 604/385.2 |
| 4,892,532 | 1/1990 | Boman | 604/366 |
| 4,900,317 | 2/1990 | Buell | 604/370 |
| 4,904,249 | 2/1990 | Miller et al. | 604/378 |
| 4,988,344 | 1/1991 | Reising et al. | 604/368 |
| 4,988,345 | 1/1991 | Reising | 604/368 |
| 5,009,651 | 4/1991 | Kamishiori et al. | 604/378 |
| 5,021,050 | 6/1991 | Iskra | 604/379 |
| 5,028,224 | 7/1991 | Pieper et al. | 425/80.1 |
| 5,037,409 | 8/1991 | Chen et al. | 604/358 |
| 5,047,023 | 9/1991 | Berg | 604/368 |
| 5,134,007 | 7/1992 | Reising et al. | 428/78 |
| 5,143,779 | 9/1992 | Newkirk et al. | 428/218 |
| 5,147,343 | 9/1992 | Kellenberger | 604/368 |
| 5,147,345 | 9/1992 | Young et al. | 604/378 |
| 5,171,391 | 12/1992 | Chmielewski et al. | 156/229 |
| 5,192,606 | 3/1993 | Proxmire et al. | 428/284 |
| 5,330,456 | 7/1994 | Robinson | 604/368 |
| 5,342,342 | 8/1994 | Kitaoka | 604/385.2 |
| 5,389,094 | 2/1995 | Lavash et al. | 604/385.2 |

FOREIGN PATENT DOCUMENTS

| | | | |
|---|---|---|---|
| 2677541 | 12/1992 | France | A61F 13/15 |
| 2699812 | 7/1994 | France | A61F 13/46 |
| 428344 | 5/1935 | United Kingdom . | |
| 511062 | 8/1939 | United Kingdom . | |
| 2101038 | 1/1983 | United Kingdom . | |
| 2237205 | 5/1991 | United Kingdom . | |
| 2266465 | 11/1993 | United Kingdom . | |
| 2266464 | 11/1993 | United Kingdom . | |
| 2270247 | 3/1994 | United Kingdom | A61F 13/15 |
| WO86/05661 | 9/1986 | WIPO . | |
| WO87/01914 | 4/1987 | WIPO . | |
| WO90/14815 | 12/1990 | WIPO . | |
| WO90/14814 | 12/1990 | WIPO . | |
| WO9110416 | 7/1991 | WIPO | A61F 13/15 |
| WO91/11164 | 8/1991 | WIPO . | |
| WO9111165 | 8/1991 | WIPO | A61F 13/52 |
| WO9301780 | 2/1993 | WIPO | A61F 13/15 |
| WO9309745 | 5/1993 | WIPO | A61F 13/46 |
| WO9311726 | 6/1993 | WIPO | A61F 13/15 |
| WO9400091 | 1/1994 | WIPO | A61F 13/15 |

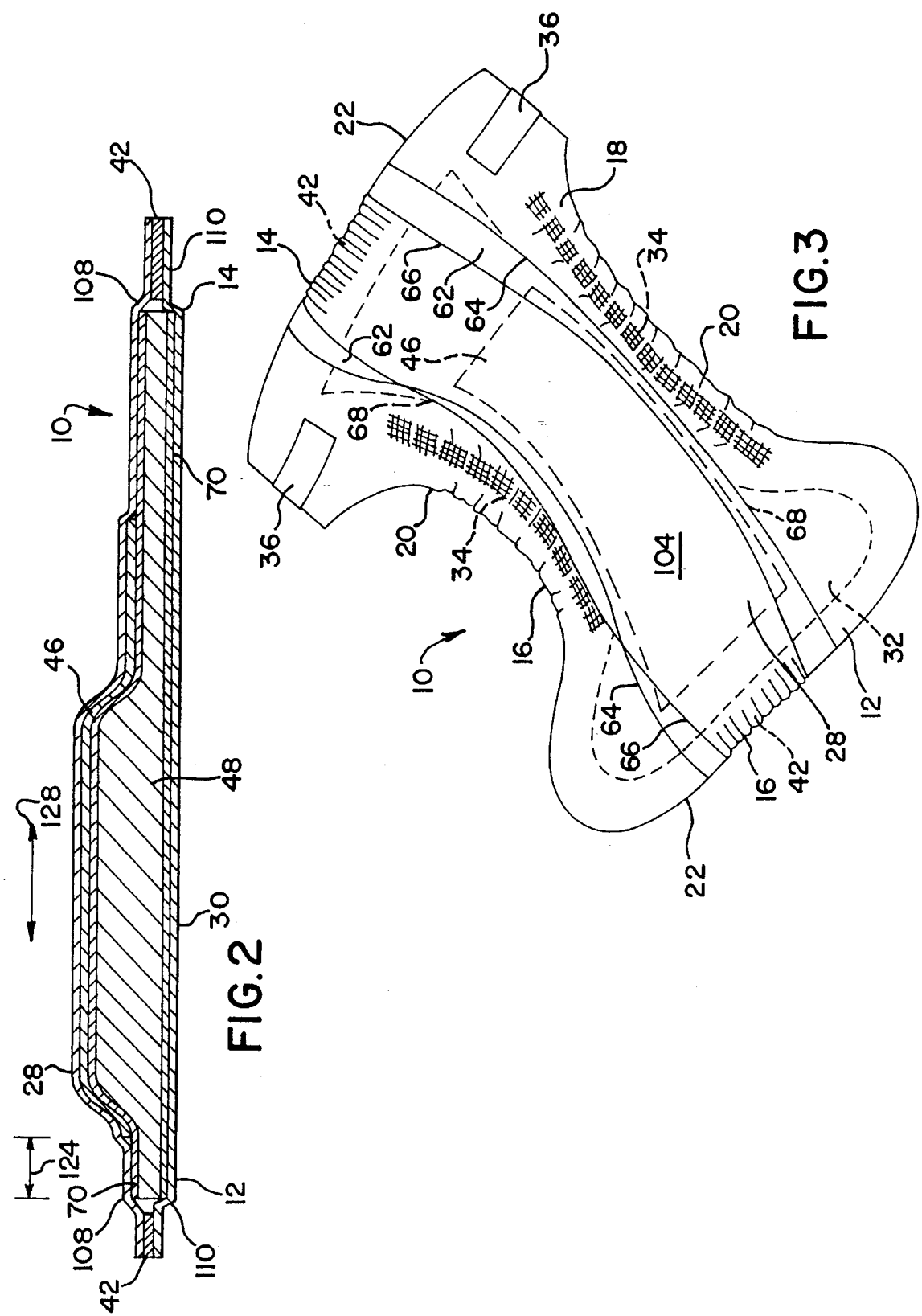

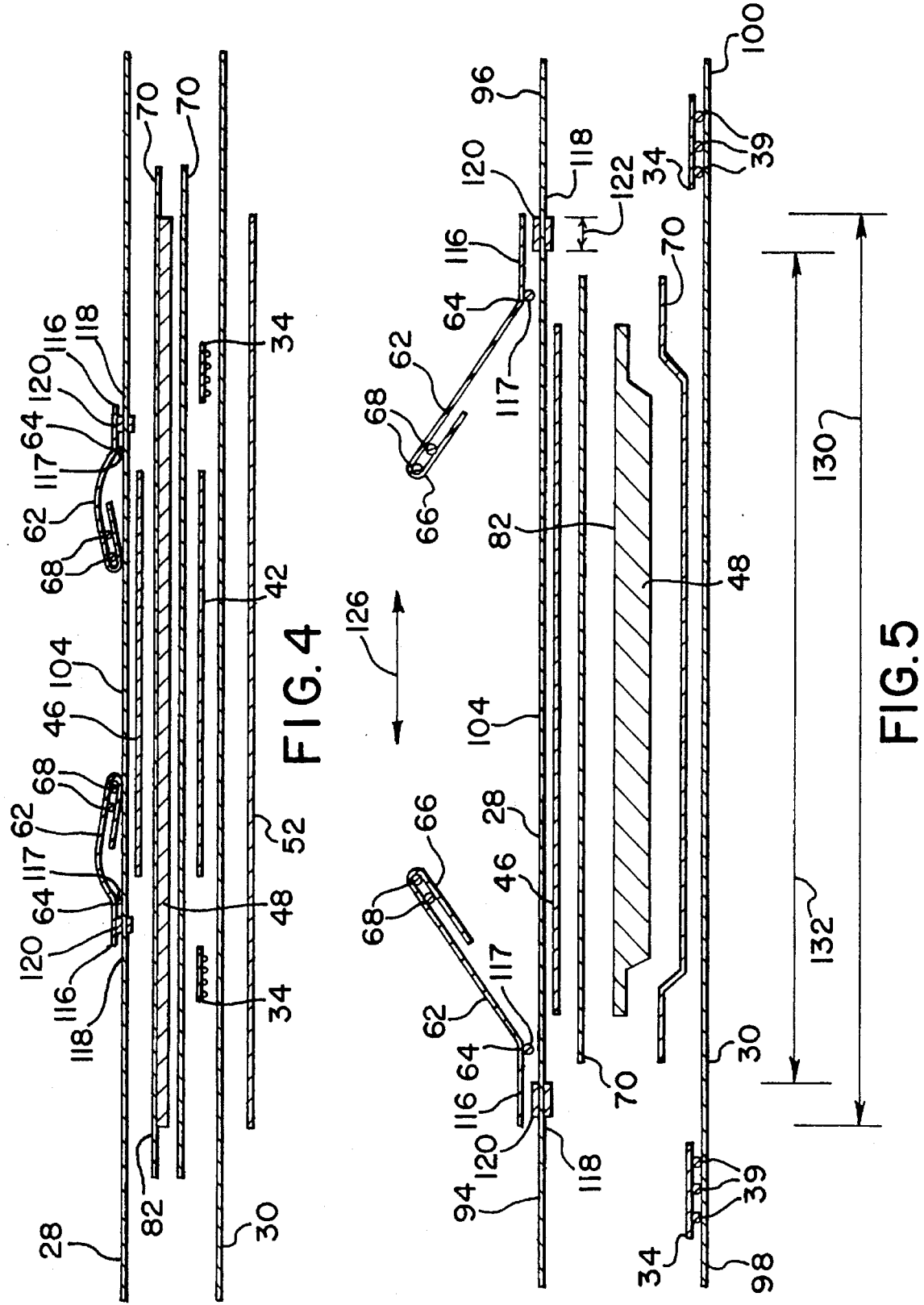

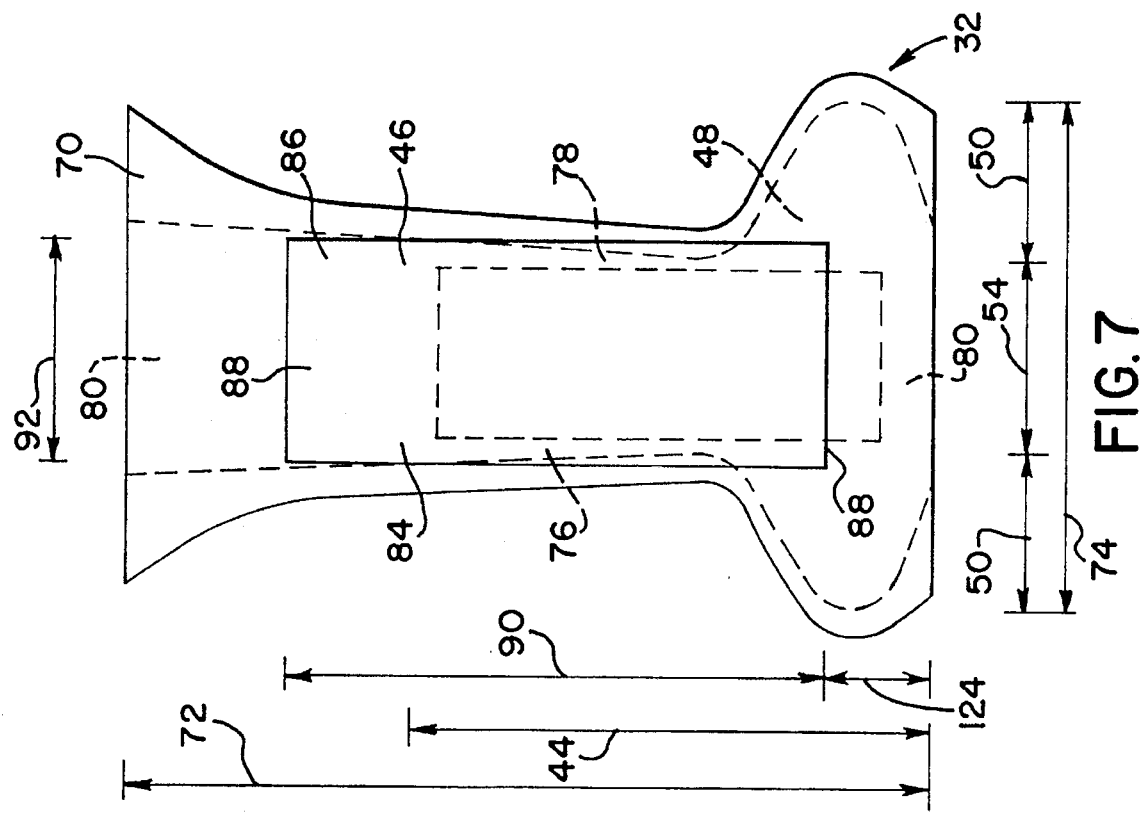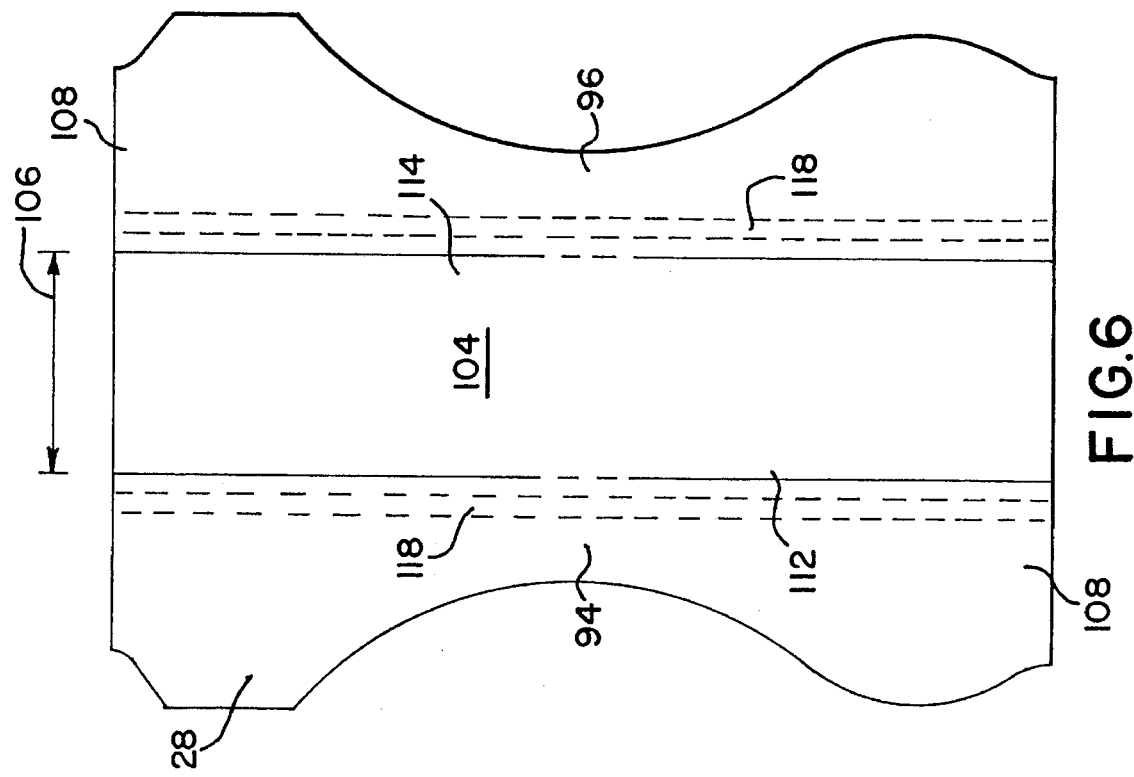

ABSORBENT ARTICLE HAVING AN IMPROVED SURGE MANAGEMENT

TECHNICAL FIELD

This invention relates to absorbent articles, particularly absorbent structures which are useful in personal care products. More particularly, the invention relates to absorbent articles which are designed for the rapid uptake, distribution and retention of repeated liquid surges into the absorbent portion of the article.

BACKGROUND OF THE INVENTION

Desired performance objectives of personal care absorbent products include low leakage from the product and a dry feel to the wearer. However, absorbent products commonly fail before the total absorbent capacity of the product is utilized. An absorbent garment, such as an incontinence garment or disposable diaper, often leaks at the leg, top-front or top-back areas of the diaper. Leakage can occur due to a variety of shortcomings in the product, one being an insufficient rate of fluid uptake by the absorbent system, especially on the second or third liquid surges.

Attempts to alleviate leakage include providing physical barriers with elastic leg gathers and changing the amount or configuration of the absorbent material at the zone of the structure into which the liquid surges typically occur. To further reduce leakage, articles with elasticized leg gathers have further incorporated additional, elasticized containment or barrier flaps located at the interior of the structure. Absorbent gelling particles have also been included to increase the liquid holding capacity in various regions of the absorbent structure.

Absorbent articles have typically employed various types of absorbent pads composed of cellulosic fibers. Particular absorbent garments have been configured to control the distribution of absorbed liquids. For example, an absorbent article can have a liquid permeable transport layer which is located between a topsheet layer and an absorbent body. In other configurations, a conventional absorbent member can have fluid storage and acquisition zones composed of cellulosic fluff mixed with absorbent gelling particles; and may include a dual-layer absorbent core arrangement comprising a bottom fluff pad containing hydrogel particles, and a top fluff pad with little or no hydrogel particles.

Non-woven materials such as carded webs and spunbonded webs, have been used as the body-side liners in absorbent products. Specifically, very open, porous liner structures have been employed to allow liquid to pass through them rapidly, and help keep the body skin separated from the wetted absorbent pad underneath the liner. Some structures have incorporated zoned surfactant treatments in preselected areas of the liners to increase the wettability of the preselected regions and thereby control the amount of liquid wet-back onto a wearer's skin. In addition other layers of material, such as those constructed with thick, lofty fabric structures, have been interposed between the liner and absorbent pad for the purpose of reducing wet-back.

With conventional fluff-based absorbent structures, such as those discussed above, the cellulosic fibers, when wetted, can lose resiliency and collapse. As a result, the liquid uptake rate of the wetted structures may become too low to adequately accommodate subsequent, successive liquid surges. Where absorbent gelling particles are incorporated between the fibers to hold them apart, the gelling particles swell and do not release the absorbed fluid. Swelling of the particles can then diminish the void volume of the absorbent structure and reduce the ability of the structure to rapidly uptake liquid.

The addition of more absorbent material, such as secondary fluff pledgets, or absorbent gelling particles, has been employed to increase holding capacity. The desired rate of liquid intake within such arrangements, however, may not be sufficiently sustained during successive liquid surges.

Despite the development of absorbent structures of the types surveyed above, there remains a need for improved absorbent structures which can adequately reduce the incidence of leakage from absorbent products, such as disposable diapers. There is a need for an absorbent structure which can provide improved handling of liquid surges and more effectively uptake and retain repeated loadings of liquid during use.

BRIEF DESCRIPTION OF THE INVENTION

Generally stated, the present invention provides a distinctive absorbent article which includes a backsheet layer and an absorbent retention portion which is superposed on the backsheet layer. The retention portion has a length and a width, and has laterally opposed side edges thereof and longitudinally opposed end edges thereof. A surge management portion is located generally adjacent a bodyside surface of the retention portion. The surge management portion is constructed to temporarily hold received liquid and release the liquid to the retention portion. The surge management portion has a width, opposed side edges thereof and opposed end edges thereof, and has a length thereof which is less than the length of the retention portion. The end edges of the surge management portion are located longitudinally inboard from the end edges of the retention portion. A porous topsheet layer is disposed in facing relation with the backsheet layer to sandwich the retention portion and the surge management portion between the backsheet layer and the topsheet layer. The topsheet layer has marginal regions thereof attached to marginal regions of the backsheet layer. The attached marginal regions of the topsheet and backsheet layers are located laterally outboard of the side edge regions of the surge management portion. A surfactant material is applied to a medial section of the topsheet layer to provide a greater wettability of the medial section, as compared to a remainder of the topsheet layer. The medial section has a width which is substantially not more than the width of the surge management portion.

Another aspect of the invention provides an absorbent article which includes a backsheet layer and an absorbent retention portion which is superposed on the backsheet layer. The retention portion has a length and a width, and has laterally opposed side edges thereof and longitudinally opposed end edges thereof. A surge management portion is located generally adjacent a bodyside surface of the retention portion. The surge management portion is constructed to temporarily hold received liquid and release the liquid to the retention portion. The surge management portion has a width, opposed side edges thereof and opposed end edges thereof, and has a length thereof which is less than the length of the retention portion. The end edges of the surge management portion are located longitudinally inboard from the end edges of the retention portion. A porous topsheet layer is disposed in facing relation with the backsheet layer to sandwich the retention portion and the surge management portion between the backsheet layer and the topsheet layer. The topsheet layer has marginal regions thereof attached to marginal regions of the backsheet layer. The attached marginal regions of the topsheet and backsheet layers are located laterally outboard of the side edge regions of the surge management portion. The surge management portion includes a fibrous nonwoven web having a basis weight of at least 20 grams per square meter, a void volume of between about 80 and about 117 cubic centimeters per gram of web at 689 dynes per square centimeter pressure, a permeability of about 8,000 to about 15,000 darcy, a porosity of about 98.6 to about 99.4 percent, and a surface area per void volume of about 10 to about 25 square centimeters per cubic centimeter.

The present invention, in its various aspects, can advantageously provide an absorbent article which has adequate absorptive capacity even though the bulk thickness and volume of the absorbent and article are quite small. The absorbent article can rapidly uptake body exudates, such as urine, and can maintain the rate of uptake even after the article has been previously wetted with one or more liquid insults. A surge management and control component of the invention can temporarily contain each liquid surge occurring in a target zone of the absorbent structure, and can further provide a more complete release and movement of the liquid into a retention portion of the structure. As a result, an absorbent garment article of the present invention can help avoid puddling of liquid against a wearer's skin and can more rapidly move the liquid away from the skin and into the absorbent structure. The more complete release of liquid into the retention portion of the absorbent structure helps to maintain a drier section of the article against the wearer. Thus, the distinctive structure of the present invention can reduce the amount of liquid held against the wearer's skin, reduce leakage of liquid from the absorbent article, and provide improved dryness and comfort to the wearer. In addition, the distinctive aspects of the present invention can be advantageously sustained during the course of multiple insults of liquid delivered into the absorbent structure.

BRIEF DESCRIPTION OF THE DRAWINGS

The invention will be more fully understood and further advantages will become apparent when reference is made to the following detailed description and accompanying drawings in which:

FIG. 2 representatively shows a length-wise, cross-sectional view taken approximately along the longitudinal centerline of the article illustrated in FIG. 1;

FIG. 3 representatively shows a perspective view of the article of the invention in which the elastic members have been allowed to contract;

FIG. 4 representatively shows a schematic, lateral, cross-sectional, exploded view taken approximately along the front waistband section of the article illustrated in FIG. 2;

FIG. 5 representatively shows a schematic, lateral, cross-sectional, exploded view taken approximately along the lateral centerline of the article illustrated in FIG. 2;

FIG. 6 representatively shows the topsheet layer employed with the present invention; and FIG. 7 representatively shows an absorbent structure employed with the present invention.

DETAILED DESCRIPTION OF THE INVENTION

Figure 1:
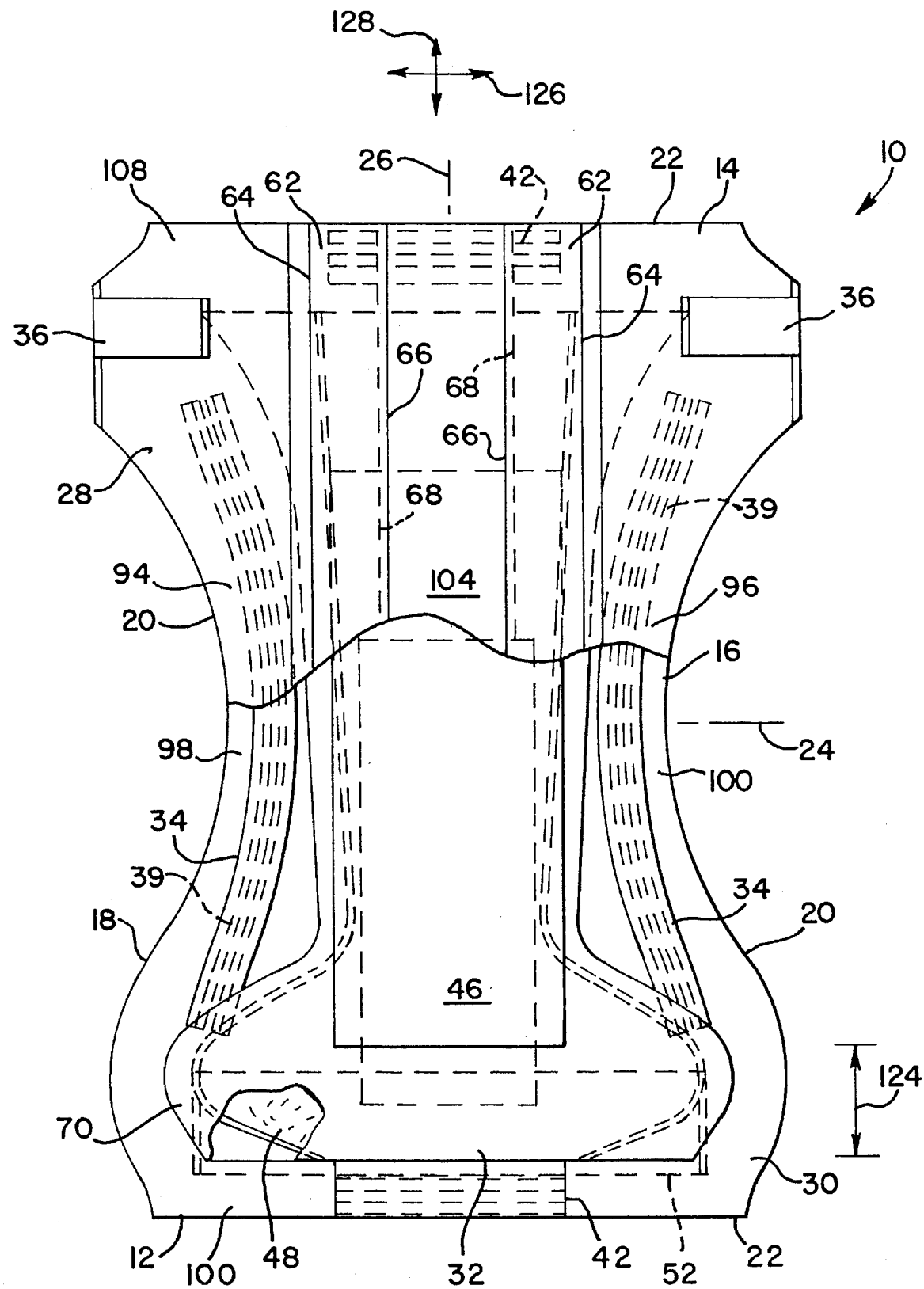
FIG. 1 representatively shows a partially cut-away, top plan view of an article of the invention.

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as adult incontinence garments, sanitary napkins, children's training pants and the like, as well as surgical bandages and sponges.

With reference to FIGS. 1, 2, 4 and 5, an absorbent article, such as diaper 10, has a cross-wise, lateral dimension 126 and a length-wise, longitudinal dimension 128. The diaper includes a backsheet layer 30 and an absorbent retention portion 48 which is superposed on the backsheet layer. The retention portion has a length 72 and a width dimension 74, and has laterally opposed side edges 76 and 78 thereof and longitudinally opposed end edges 80 thereof. A surge management portion 46 is located generally adjacent a bodyside surface 82 of the retention portion 48. The surge management portion is constructed to temporarily hold received liquid and release the liquid to the retention portion. The surge management portion has opposed side edges 84 and 86 thereof and opposed end edges 88 thereof, and has a length 90 thereof which is less than the length 72 of the retention portion 48. The end edges 88 of the surge management portion 46 are located longitudinally inboard from the end edges 80 of the retention portion 48. A porous topsheet layer 28 is disposed in facing relation with the backsheet layer 30 to sandwich the retention portion 48 and the surge management 46 between the backsheet layer and the topsheet layer. Topsheet layer 28 has marginal regions, such as marginal regions 94 and 96, thereof, attached to marginal regions such as marginal regions 98 and 100, of the backsheet layer 30. The attached marginal regions of the topsheet and backsheet layers are located laterally outboard of the side edge regions 84 and 86 of the surge management portion 46. A surfactant material, such as a selected wetting agent, is applied to a medial section 104 of the topsheet layer 28 to provide a greater wettability of the medial section, as compared to a remainder of the topsheet layer 28. The medial section 104 has a width 106 (FIG. 6) which is substantially not more than the width 92 (FIG. 7) of the surge management portion 46. In particular arrangements the medial section width 106 can be substantially equal to the width 92 of the surge management portion.

In particular embodiments of the invention, the surge management layer can be arranged to provide a surge layer basis weight within the range of about $20 \leq 102$ gsm, and can comprise nonwoven fabrics, such as spunbond webs, airlaid webs and bonded-carded webs, composed of synthetic polymer fibers. Suitable fibers include, for example, polyester fibers, polyester/polyethylene bicomponent fibers, polypropylene/polyethylene bicomponent fibers and the like, as well as blends and other combinations thereof.

In other aspects of the invention, the surge management portion can be characterized by various distinctive structural parameters. Such parameters include, for example, resiliency and bulk recovery, basis weight, porosity, void volume, surface area per void volume (SA/VV), saturation capacity, and permeability.

FIG. 1 is a representative plan view of diaper 10 of the present invention in its flat-out, uncontracted state (i.e., with all elastic induced gathering and contraction removed). The diaper article has a cross-directional, lateral dimension 126 and a longitudinal, length dimension 128. Portions of the structure are partially cut away to more clearly show the interior construction of diaper 10, and the surface of the diaper which contacts the wearer is facing the viewer. In the shown embodiment, diaper 10 has a front waistband region 12, a back waistband region 14, an intermediate crotch region 16 which interconnects the front and rear waistband regions. The outer edges of the diaper define a periphery 18 in which the longitudinally extending side edge margins are designated 20 and the laterally extending end edge margins are designated 22. Preferably, the side edges are curvilinear and contoured to define leg openings for the diaper. The end edges are shown as straight, but optionally, may be curvilinear. The diaper additionally has a transverse center line 24 and a longitudinal center line 26.

Diaper 10 typically includes a porous, liquid permeable topsheet 28; a substantially liquid impermeable backsheet 30; an absorbent pad, such as absorbent structure 32, positioned between the topsheet and backsheet; and elastic members, such as leg elastics 34 and waist elastics 42. Topsheet 28, backsheet 30, absorbent structure 32, and the elastic members 34 may be assembled in a variety of well-known diaper configurations.

In the illustrated embodiment, two containment flaps 62 are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference to the extent that it is consistent (not contradictory) herewith.

Containment flaps 62, in the shown arrangement, are attached to topsheet layer 28 along length-wise extending fixed regions, such as fixed edges 64, of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. In the shown embodiment, for example, the moveable edge of the barrier flap is connected to the flap elastics by partially doubling the flap material back upon itself by a limited amount which is sufficient to enclose flap elastics 68. The containment flaps may, for example, be constructed of a fibrous material which is similar to the material comprising topsheet 28, or similar to the material comprising surge management portion 46. Other conventional materials, such as polymer films, may also be employed.

With reference to FIGS. 4 and 5, at least a pair of containment or barrier flaps 62 are connected to laterally opposed, longitudinally extending regions of topsheet layer 28, and the connected topsheet regions are located substantially adjacent to laterally opposed side edge regions 112 and 114 (FIG. 6) of the topsheet medial section 104. The connected topsheet regions are also located substantially laterally inboard of the elasticized side margins of the diaper article 10. In particular aspects of the invention, the connected regions of topsheet layer 28 are located laterally outboard of the side edge regions of the topsheet medial section 104. In other aspects of the invention, barrier flaps 62 are constructed of a material which is permeable to gas, such as ambient air. Alternative configurations of the invention can include barrier flaps which are constructed of a material which is resistant to a passage of aqueous liquid, such as urine, therethrough. For example, barrier flaps 62 may be constructed of a spunbond-meltblown-spunbond (SMS) laminate material. In the illustrated embodiment, for example, the barrier flaps can be constructed of a SMS material having a basis weight of about 0.85 osy (about 28 gsm). The spunbond layers are composed of polypropylene fibers, and the meltblown layer is composed of meltblown polypropylene fibers.

In the various aspects of the invention, barrier flaps 62 can be configured to be permeable to gas while having limited permeability to aqueous liquid. Particular configurations of the barrier flaps 62 can, for example, have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated 31 Dec. 1968.

With reference to FIGS. 4 and 5, each of the barrier flaps 62 can include a laterally extending base section 116 thereof with at least a portion of the base section attached to the topsheet layer 28 at a topsheet securement section 118, which is located laterally outboard of the retention portion 48 and laterally outboard of the surge management portion 46. The topsheet securement section 118 of topsheet layer 28 is operably sealed to the backsheet layer 30 to substantially prevent or block a leakage of liquid through the securement section 118. The securement section can be constructed by employing various conventional techniques, such as adhesive bonding, thermal bonding, sonic bonding, stitching, stapling, or the like. The illustrated embodiment, for example, is configured with the topsheet securement section 118 sealed to the backsheet layer 30 with a strip of adhesive, such as a pressure sensitive hot melt adhesive. In the various configurations of the invention, the adhesive can be configured in a desired regular or irregular pattern. A particular aspect of the invention can, for example, be configured to seal the topsheet securement section 118 to backsheet 30 with a substantially continuous adhesive bead or strip 120. Other aspects of the invention can be configured with the adhesive strip 120 having a cross-directional width 122 which is within a range of about 1–7 millimeters. Alternatively, the adhesive strip can have a width within the range of about 1–5 mm, and optionally can have a width within the range of about 2–3 mm.

The adhesive strip can advantageously be configured to provide a barrier bead which extends generally length-wise of the diaper. Accordingly, at least a portion of the barrier bead is located in the diaper crotch region 16. At least the crotch portion of the barrier bead can advantageously be constructed to operably bond and substantially seal the corresponding portion of the securement section 118 of topsheet layer 28 to both the barrier flap base section 116 and the backsheet layer 30 by effectively "bleeding" through the topsheet layer 28 to make operable contact with the backsheet layer. When a substantially continuous seal is provided, liquid can be more effectively contained between the two flaps 62. To provide a more effective barrier bead, the representative adhesive strip 120 is wiped or otherwise applied onto the appointed section of the flap base 116 at a position which interposes the strip between the terminal side edge of tissue wrap 70 and the leg elastic carrier sheet. Additional pressure can be applied to the adhesive strip area to help assure a desired seal.

At least a portion of the base section can also be attached to the topsheet layer 28 along a topsheet seam section located along the fixed edge 64 of the containment flap. A suitable connecting means, such as a substantially continuous adhesive bead 117, operably secures the fixed barrier flap edge to the topsheet seam section. The shown embodiment of the seam section is positioned laterally inboard of the associated securement section 118, and is located proximate the juncture between the flap base section 116 and the relatively upstanding portion of the barrier flap.

As illustrated by the shown embodiment of diaper 10, topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery 18 of diaper 10. The periphery delimits the outer perimeter of the diaper 10, and in the illustrated embodiment, comprises laterally marginal end edges 22, and contoured longitudinally extending marginal side edges 20. The diaper 10 has front and back waistband regions 12 and 14, respectively, extending from the laterally extending end edges 22 of diaper periphery 18 toward the transverse center line 24 of the diaper along a distance of from about 2 percent to about 10 percent of the overall length of diaper 10. The waistband regions comprise those upper portions of diaper 10, which when worn, wholly or partially cover or encircle the waist or mid-lower torso of the wearer. The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surge typically occur in diaper 10 or other disposable absorbent article.

Topsheet 28 presents a body-facing surface which is compliant, soft-feeling, and non-irritating to the wearer's skin. Further, topsheet 28 can be less hydrophilic than retention portion 48, and is sufficiently porous to be liquid permeable, permitting liquid to penetrate through its thickness. The topsheet layer has marginal side regions 94 and 96, and has marginal end regions 108.

A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 22 gsm and density of about 0.06 gm/cc. The fabric can be surface treated with a selected amount of surfactant, such as about 0.28% Triton X-102 surfactant. The surfactant can be applied by any conventional means, such as spraying, printing, brush coating or the like.

With reference to FIG. 6, the surfactant material, such as a conventional wetting agent, can be applied to a medial section 104 of the topsheet layer 28 to provide a greater wettability of the medial section, as compared to a remainder of the topsheet layer 28. In particular configurations, the width 106 of the medial section 104 can be substantially equal to or less than the width 92 of the surge management portion 46. In alternative configurations, the medial section width 106 can be substantially equal to or less than a cross-directional spacing 132 between the pair of adhesive strips 120 employed at the topsheet securement sections 118 (FIG. 5).

In other aspects of the invention, the surfactant-treated topsheet medial section 104 can have a width 106 which is not less than about 64 millimeters. Alternatively, the medial section width 106 can be not less than about 76 millimeters, and optionally, can be not less than about 89 millimeters to provide desired benefits. Other configurations of the invention can have a medial section width 106 which is not more than about 254 millimeters. Alternatively, the medial section width is not more than about 152 millimeters, and optionally, is not more than about 114 millimeters to provide desired performance. In a particular embodiment of the invention, for example, the surfactant-treated topsheet medial section 104 can have a width of about 102 millimeters.

In further aspects of the invention, the appointed medial section 104 of topsheet layer 28 can have a medial section width 106 which is within a range of about 25–100 percent of the cross-directional spacing 132 between adhesive barrier strips 120. Desirably, the medial section width 106 is about 80 percent of the cross-directional spacing between the adhesive barrier strips.

The medial section can be approximately centered with respect to the longitudinal centerline of the diaper, and in the shown embodiment extends along substantially the entire length of the topsheet layer. Alternatively, the surfactant treated medial section can be constructed to extend along only a predetermined portion of the topsheet length.

The various configurations of the invention can also be arranged with the topsheet medial section 104 constructed with a width which is not more than, and alternatively can be less than, a lateral spacing 130 between the topsheet securement sections 118 (FIG. 5). As a result, the width 106 of the surfactant-treated medial section can be not more than, and alternatively can be less than, a lateral spacing 132 between the adhesive sealing strips 120. Accordingly, each topsheet securement section 118 can be positioned laterally outboard from its corresponding, proximately located side edge region of medial section 104. Similarly, each adhesive strip 120 can be positioned laterally outboard from its corresponding, proximately located side edge region of the topsheet medial section 104.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10. The backsheet layer has marginal side regions 98 and 100, and has marginal end regions 110.

In particular embodiments of the invention, backsheet 30 is a polyethylene film having a thickness of from about 0.012 millimeters (0.5 mil) to about 0.051 millimeters (2.0 mils). In the shown embodiment, the backsheet is a film having a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. Backsheet 30 typically provides the outer cover of the article. Optionally, however, the article may comprise a separate outer cover member which is in addition to the backsheet.

Backsheet 30 may optionally be composed of a microporous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise be provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 2.5 centimeters (about 0.5 to 1.0 inch), to provide side margins.

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30.

It should be readily appreciated that the above-described attachment means may also be employed to interconnect and assemble together the various other component parts of the article described herein.

In the representatively shown embodiment of the invention, the topsheet layer 28 is disposed and secured in facing relation with the backsheet layer 30 to retain and hold the retention portion 48 and the surge management 46 between the backsheet layer and the topsheet layer. The marginal side regions 94 and 96 of topsheet layer 28 are operably connected to corresponding marginal side regions 98 and 100, respectively, of the backsheet layer 30. Each of the attached marginal side regions of the topsheet and backsheet layers is located laterally outboard of its corresponding, associated side edge region 84 or 86 of the surge management portion 46. In particular configurations of the invention, the attached marginal regions of topsheet 28 can include marginal end regions 108. The attached marginal end regions are located longitudinally outboard of the end edge regions 88 of the surge management portion 46. Similarly, the attached marginal regions of backsheet 30 can include attached marginal end regions 110, which can be located longitudinally outboard of the end edge regions 88 of the surge management portion 46.

Fastening means, such as tape tab fasteners 36, are typically applied to the back waistband region 14 of diaper 10 to provide a mechanism for holding the diaper on the wearer. Tape tab fasteners 36 can be any of those well known in the art, and are typically applied to the corners of diaper 10. For example, adhesive fasteners, mechanical fasteners, hook and loop fasteners, snaps, pins or buckles, may be used alone, or in combination. In the shown configuration, the fasteners are adhesive fasteners, which are constructed to releasably adhere to a landing zone patch 52 attached to the front waistband section of the diaper to provide a refastenable adhesive fastening system.

Elastic members 34 are disposed adjacent the periphery 18 of diaper 10 along each of the longitudinal side edges 20. The leg elastic members 34 can be connected to either or both of the topsheet and backsheet layers to provide elasticized side margins of the diaper article, and can be arranged to draw and hold diaper 10 against the legs of the wearer. Waist elastic members 42 may also be disposed adjacent either or both of the end edges of diaper 10 to provide elasticized waistbands.

Elastic members 34 and 42 are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their unrelaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34 and 42 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are nonparallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt or other type of adhesive.

In the illustrated embodiments of the invention, for example, leg elastic members 34 may comprise a carrier sheet to which are attached a grouped set of elastics composed of a plurality of individual elastic strands 39. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer available from DuPont, a business having offices in Wilmington, Del. Each elastic strand is typically within the range of about 620–1050 decitex (dtx), and preferably, is about 940 dtx in an embodiment of the invention wherein three strands are employed for each elasticized legband. In addition, leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. As representatively shown in FIG. 1, the curved elastics may have an inwardly bowed and outwardly bowed, reflex-type of curvature, and the length-wise center of the elastics may be offset by a selected distance within the range of about 0–8 cm toward either the front or rear waistband of the diaper to provide desired fit and appearance. In particular embodiments of the invention, the innermost point (apex) of the set of curved elastics can be offset about 0–12 cm towards the front or rear waistband of the diaper, and the outwardly bowed reflexed-portion can be positioned toward the diaper front waistband.

An absorbent body, such as absorbent structure 32, is positioned between topsheet 28 and backsheet 30 to form diaper 10. The absorbent body has a construction which is generally compressible, conformable, non-irritating to the wearer's skin, and capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

In the embodiment representatively shown in FIG. 7, absorbent structure 32 includes a liquid-acquisition, target zone 44, and has a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions 50 and a central region 54. Target zone 44 encompasses the area where repeated liquid surges typically occur in absorbent structure 32. The particular location where liquid is discharged, such as during urination, can vary depending on the age and gender of the wearer. For example, male infants tend to urinate further toward the front end of the diaper. The female target zone is located closer to the center of the crotch. As a result, the shape and relative longitudinal placement of surge management portion 46 can be selected to best correspond with the actual target zone of either or both categories of wearers. Generally stated, the target zone is a section of absorbent structure 32 which is located in the front 60% of the length of the absorbent structure. With reference to the percentage of the total length of absorbent structure 32 measured into the absorbent structure from the front waistband edge thereof, the target zone may preferably comprise a region which begins at a line positioned approximately 10% of the absorbent structure length away from the front waistband edge and ends at approximately 60% of the absorbent structure length away from the front waistband edge.

The ear regions 50 comprise portions which generally extend inwardly from the outermost lateral side edges of the absorbent structure toward its longitudinal center line. Thus, when the diaper is worn, the ear regions are configured to generally engage the sides of the wearer's waist and torso, and central region 54 is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

In a particular aspect of the invention, the absorbent structure has an absorbent capacity of at least about 300 gm of synthetic urine. Alternatively, the absorbent structure can have an absorbent capacity of at least about 400 gm of synthetic urine to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System. When measured with this system in accordance with the procedure described in detail herein below, fibers having contact angles less than 90° are designated "wettable" or hydrophilic, while fibers having contact angles greater than 90° are designated "nonwettable" or hydrophobic.

Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference to the extent that it is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al. and entitled "ABSORBENT COMPOSITES AND ABSORBENT ARTICLES CONTAINING SAME" (Attorney Docket No. 10174), which was filed on Sep. 11, 1991 and is hereby incorporated by reference to the extent that it is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. patent application Ser. No. 184,302 of S. Kellenberger and entitled "ABSORBENT PRODUCTS CONTAINING HYDROGELS WITH ABILITY TO SWELL AGAINST PRESSURE" (Attorney Docket No.

8786); European Patent Application EP 0 339 461A1, published Nov. 2, 1989; the disclosure of which is hereby incorporated by reference to the extent that it is consistent with the present specification.

An example of superabsorbent polymer suitable for use in the present invention is SANWET IM 3900 polymer available from Hoechst Celanese, a business having offices in Portsmouth, Va. Other suitable superabsorbents may include W45926 polymer obtained from Stockhausen, a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desireable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–900 gsm. Again, such basis weight is particularly desireable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 includes 4–22 grams of wood pulp fluff, preferably includes about 8–14 grams of fluff and more preferably includes about 10–12 grams of fluff to provide desired benefits. The wood pulp fluff generally provides shape and form to diaper 10, and carries and positions the particles of superabsorbent polymer or other high-absorbency material. Retention portion 48 can contain about 7–12 grams of superabsorbent polymer, and in the shown embodiment, contains about 8.5 grams of superabsorbent polymer. Sufficient superabsorbent polymer is incorporated into retention portion 48 to provide an adequate total absorbent capacity of at least about 300 gm of urine. For example, a medium size diaper for an infant weighing about 13–23 lb can typically have a total retention capacity of about 500 grams of urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 3.5–4.5 inches in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 issued Jul. 2, 1991 to C. Pieper et al., and entitled "METHOD AND APPARATUS FOR INTERMITTENTLY DEPOSITING PARTICULATE MATERIAL IN A SUBSTRATE" (Attorney Docket No. 8761), the disclosure of which is hereby incorporated by reference to the extent that it is consistent herewith.

In a particular aspect of the invention, absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 9.0 inches, the narrowest portion of the crotch section has a width of about 3.5 inches and the back waistband region has a width of about 4.5 inches.

With reference to FIGS. 2 and 7, the entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

At least the bodyside layer of wrap sheet 70 has a pore distribution wherein no more than about 5 percent of the pores, as measured by Coulter porometry, are greater than about 50 micrometers in diameter. For example, the complete wrap sheet 70, or at least the bodyside layer of the wrap sheet, may comprise a meltblown web composed of meltblown polypropylene fibers having a fiber size of about 5 micrometers and arranged to form a basis weight within the range of about 8–20 gsm.

Another example of absorbent wrap 70 may comprise a low porosity cellulosic tissue web composed of an approximately 50/50 blend of hardwood/softwood fibers. The tissue has a 13 lb basis weight at the reel and a porosity of about 90 cfs/sq. ft. Similar to the meltblown wrap sheet material, the entire tissue wrapsheet material, or at least the bodyside layer thereof, has not more than about 5 percent of its pores greater than about 50 micrometers in diameter. Preferably, not more than about 1 percent of the pores are greater than 50 micrometers in diameter.

Absorbent wrap 70 may comprise a multi-element wrapsheet which includes a separate bodyside wrap layer and a separate outerside wrap layer, each of which extends past all or some of the peripheral edges of retention portion 48, as representatively shown in FIGS. 2 and 7. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, the bodyside and outerside layers of absorbent wrap 70 extend at least about ½ inch beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

To provide the bonding between the bodyside and outerside portions of absorbent wrap 70, an adhesive, such as National Starch 72-3723 adhesive, can be printed onto the appointed bonding areas 74 of the absorbent wrap with, for example, a rotogravure-type system. The adhesive is available from National Starch and Chemical Co., a business having offices in Bridgewater, N.J., and rotogravure-type adhesive applicators are available from Egan Machinery Division, a business having offices at Oconto Falls, Wis. Retention portion 48 can then be placed between the bodyside and outerside portions of absorbent wrap 70, and the mating edges of the absorbent wrap portions can be bonded together to provide a generally complete peripheral seal along substantially the entire perimeter of the retention portion 48. In the illustrated embodiment, the adhesive is applied at an add-on rate of about 5 grams of solids per square meter of bonding to attach together the lapping edges of the bodyside and outerside portions of absorbent wrap 70.

With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over three insults of liquid into the absorbent structure. The addition of a layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, and to transport the liquid from its initial entrance point to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

Surge management portion 46 can have a generally uniform thickness and cross-sectional area. Alternatively, a configuration can be used wherein the bodyside surface area of the surge management portion is greater or less than the surface area of a section taken along an X-Y plane located below the bodyside surface of the surge management portion.

The absorbent article represented by diaper 10 can include a surge management portion 46 which is arranged in a direct, contacting liquid communication with an adjacent absorbent retention portion 48. As representatively shown in FIGS. 2 and 4, surge management portion 46 may be configured for placement adjacent an outwardly facing, outerside of topsheet 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

In the various embodiments of the invention, at least a major part of surge management portion 46 is located within target zone 44, and optionally, the surge management portion can have an areal extent which extends completely over target zone 44. Retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to eventually release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in target zone 44, however, the particles can cause the structure to retain and hold unacceptably high amounts of the liquid. In addition, the transport of liquids away from target zone 44 to other sections of absorbent structure 32, particularly retention portion 48, can be undesirably impaired.

As mentioned previously, surge layer 46 can be a separately formed layer, which lies adjacent the outwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in the generally sideways (X-Y) direction.

A capillary force differential created at the interface between the retention portion 48 and the material immediately adjacent the bodyside of the retention portion can improve the containment characteristics of absorbent structure 32. For example, if the surge management portion is composed of layer 46 positioned immediately adjacent to the retention portion, and if the surge layer is appropriately configured to provide and maintain a relatively lower capillary attraction, as compared to the capillary attraction exhibited by retention portion 48, then liquid surges occurring in target zone 44 tend to be desorbed more readily from the surge management portion and into the retention portion. Because retention portion 48 can thereby have a relatively higher capillarity than surge management portion 46, the liquid surges tend to be drawn into retention portion 48 and distributed to the more remote regions thereof by wicking along the plane generally defined by the retention portion.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various aspects of the invention, the surge management portion length 90 is not less than about 165 millimeters. Alternatively, the surge management portion length is not less than 191 millimeters, and optionally, is not less than about 216 millimeters. Other aspects of the invention can be configured with the length 90 of surge management portion 46 configured to be not more than about 343 millimeters. Alternatively, the surge management portion length 90 can be not more than about 318 millimeters, and optionally can be not more than about 292 millimeters. With an embodiment of the invention having a retention portion length of about 16.5 inches (419 millimeters), the surge management portion length 90 can be about 9 inches (229 millimeters) for diapers configured for male infants, and about 11 inches (279 millimeters) configured for female infants.

In particular aspects of the invention, the surge management portion can have a length 90 which is not less than about 40 percent of the length of retention portion 48. Alternatively, the surge management portion length can be not less than about 46 percent, and optionally can be not less than about 52 percent of the length of retention portion 48. In other aspects of the invention, the surge management portion length 90 can be not more than about 82 percent of the length of retention portion 48. Alternatively, the surge management portion length can be not more than about 76 percent, and optionally, can be not more than about 70 percent of the length of retention portion 48.

The various embodiments of surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within front section 40 of absorbent structure 32. Thus, surge management portion 46 can be approximately centered about the longitudinal center line 58 of absorbent structure 32, and positioned primarily in central region 54 of front section 40 of absorbent structure 32. In the illustrated embodiment, for example, none of surge management portion 46 is located in ear regions 50. In addition, at least about 50% of the length of the surge management portion is located in the front half of the absorbent structure.

In particular aspects of the invention, the length 90 of the surge management portion 46 is not more than about 85 percent of the length 72 of the retention portion 48. Alternatively, the surge management portion length is not more than about 70 percent of the retention portion length 72, and optionally is not more than about 55 percent of the retention portion length.

In other aspects of the invention, the end edges 88 of the surge management portion can be spaced longitudinally inboard from the end edges 80 of the retention portion 48.

In particular configurations of the invention, the corresponding, relatively adjacent front end edge of surge management portion 46 can be spaced a predetermined discrete distance from a front waistband end edge of the retention portion 48. With reference to FIG. 7, for example, a front edge spacing 124 between the corresponding front end edges of surge management portion 46 and retention portion 48 can be configured with a front spacing 124 which is not less than about 5 millimeters. Alternatively, the front edge spacing 124 is not less than about 13 millimeters, and optionally is not less than about 25 millimeters, to provide desired benefits. In further aspects of the invention, the front edge spacing 124 is not more than about 76 millimeters. Alternatively, the front edge spacing 124 is not more than about 64 millimeters, and optionally, is not more than about 51 millimeters to provide desired performance.

For example, in an embodiment of the invention having a retention portion length of about 419 millimeters, the front end edge of surge management portion 46 can be spaced from the front end edge of retention portion 48 by a spacing distance of about 2 inches (about 51 millimeters) when the diaper is configured for male infants. For a diaper configured for female infants, the front end edge of surge management portion 46 can be spaced from the front end edge of retention portion 48 by a distance of about 1 inch (about 25 millimeters).

It has been found that an effective fabric for constructing the surge management portion can be distinctively characterized by particular distinctive parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure. In particular configurations of the invention, the surge material can include bicomponent fibers. For example, polypropylene/polyethylene bicomponent fibers may be employed to form the bicomponent fiber portion of any of the described fabrics. In addition, the bicomponent fibers may be flat crimped or helically crimped.

In particular aspects of the invention, the fibrous nonwoven web comprising surge management portion 46 can be a bonded, uniformly mixed, single layer structure having a basis weight of at least 20 grams per square meter, a void volume between about 40 and 60 cubic centimeters per gram of web at a pressure of 689 dynes per square meter (0.01 psi), a permeability of about 5,000 to about 8,000 darcy, a porosity of about 97.2% to about 98.8% and a surface area per void volume of about 24 to about 49 square centimeters per cubic centimeters. The web fibers may be thermoplastic, and may be heat bonded to one another. In addition, the web structure can have a density within a range of about 0.017–0.025 gm/cc, as determined at a pressure of 689 dynes per square meter (0.01 psi).

For example, the surge management portion may include a substantially homogeneous single-layer fibrous nonwoven web having a basis weight of about 48.8 gsm created by using about 40 percent by weight of a Hoechst Celanese type 295 6.0-denier polyester fibers and 60 percent by weight of a BASF 3.0-denier polyethylene sheath/polyester core bicomponent fibers. The homogeneous blend of fibers were bonded together using hot air passed through the web mass at a temperature of 135° C. for approximately 4 seconds. The resultant web exhibited a void volume of about 52 cc/gm, a SA/VV value of about 29.9 cm$^2$/cc, a porosity of about 98.5%, a permeability of about 6925 darcy, a saturation capacity of about 44 gm/gm, a wet compression resilience of about 81%, and a dry compression resilience of about 86%.

In other aspects of the invention, the fibrous nonwoven web can be made from or include a plurality of fibers bonded to one another to form a lofty nonwoven web having a basis weight of at least 20 grams per square meter. In more refined embodiments the basis weight can range from about 40 to about 68 grams per square meter. The web can be made entirely from bicomponent fibers which are typically crimped and which will generally have a fiber denier equal to or greater than 2 denier. Alternatively, the web can be made from a combination of fibers such as bicomponent fibers and polyester fibers. In such embodiments, the web will usually include at least 50 percent by weight of bicomponent fibers. The resultant web will have a void volume of between about 80 and about 117 cubic centimeters per gram of web at 689 dynes per square centimeter pressure, a permeability of about 8,000 to about 15,000 darcy, a porosity of about 98.6 to about 99.4 percent, a surface area per void volume of about 10 to about 25 square centimeters per cubic centimeter, a saturation capacity between about 55 and about 80 grams of 0.9 percent saline solution per gram of web and a compression resilience in both the wet and dry state of at least 60 percent. In addition, the web structure can have a density within a range of about 0.008–0.013 gm/cc, as determined at a pressure of 689 dynes per square meter (0.01 psi).

For example, the surge management portion can include a single layer fibrous nonwoven web having a basis weight of about 49.8 gsm created by using a uniform mixture of 40 percent by weight of a Hoechst Celanese type 224, 6.0-denier polyester staple fibers and 60 percent by weight of a Chisso-type ES P, 3.0-denier by 38 millimeter polypropylene sheath/polypropylene core bicomponent fiber. The web was bonded using hot air at a temperature of 135° C. for approximately 4 seconds. The resultant web exhibited a void volume of about 84 cc/gm, a SA/VV value of about 20 cm$^2$/cc, a porosity of about 98.9%, a permeability of about 9256 darcy, a saturation capacity of about 59 gm/gm, a wet compression resilience of about 76%, and a dry compression resilience of about 76%.

As another example, a substantially homogeneous single-layer fibrous nonwoven web having a basis weight of 51.9 gsm was created by using 20 percent by weight of a Hoechst Celanese type 295, 6.0-denier polyester fibers; 20 percent by weight of a Hoechst Celanese type 183, 1.5 denier polyester fibers and 60 percent by weight of a BASF 3.0-denier polyethylene sheath/polyester core bicomponent fibers. The homogeneous blend of fibers was bonded together using hot air at a temperature of 135° C. for approximately 4 seconds. The resultant web exhibited a void volume of about 110 cc/gm, a SA/VV value of about 16.2 cm$^2$/cc, a porosity of about 99.3%, a permeability of about 13,189 darcy, a saturation capacity of about 79 gm/gm, a wet compression resilience of about 73%, and a dry compression resilience of about 70%.

The amount of basis weight can be important for providing a total holding capacity which is adequate to temporarily retain the amount of liquid that is typically discharged by a wearer during a single surge/insult of liquid into the absorbent article.

It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends. The surge management material employed with the present invention will be at least about 20 grams per square meter with no real upper limit, with the target range being from about 40 to about 68 grams per square meter.

The void volume of the fibrous nonwoven web is a measure of how much air space is present in the structure. The void volume is measured at 689 dynes per square centimeter (0.01 pounds per square inch), and will range from about 80 to about 117 cubic centimeters per gram of web with the target range being from about 80 to about 100 cubic centimeters per gram of web. Void volume is the web's specific volume minus the fiber's specific volume. For the purposes of the present invention, the specific volume is measured by a compression test at 0.01 psi (with an INSTRON or SINTECH testing apparatus). For the surge materials employed with the present invention, the void volume may approximately equal the specific volume since the fiber specific volume is much less than the web specific volume.

The permeability of the surge material structure indicates the ability of the structure to conduct a liquid through the material. When a liquid initially enters a surge structure, liquid movement is dominated by forced flow from the momentum of the fluid. Capillarity may not be significant in this flow regime as it may not have enough time to control the liquid path, thus, liquid flow through the structure will be controlled by the permeability of the structure on the initial insult. A high permeability value indicates that it is relatively easy for a liquid to flow through the structure. Permeability for the materials according to the present invention will range between about $7.8 \times 10^{-5}$ to about $1.5 \times 10^{-4}$ square centimeters (8,000 to 15,000 darcy). Outside this range other materials have been found not to work as well. Permeability for surge materials has been found to be related to; the web's void volume, porosity ($\phi$) and fiber surface area per void volume (SA/VV).

The porosity of the nonwoven web is the ratio of the amount of void space in a web to the total volume of the web. The porosity of the surge management materials employed with the present invention, as measured at a pressure of 689 dynes per square centimeter (0.01 pounds per square inch), will range from about 98.6% to about 99.4%. Porosity is one minus the ratio of the web density ($\rho_{web}$) divided by the fiber density ($\rho_{fiber}$); or $\phi=1-(\rho_{web}/\rho_{fiber})$. The web density is measured by a compression test at 689 dynes per square centimeter (0.01 psi) load.

The surface area per void volume, with the void volume being measured at 689 dynes per square meter (0.01 pounds per square inch) pressure, will range from about 10 to about 25 square centimeters per cubic centimeter. Permeability is the result of fluid having to travel over and around fiber surfaces when under forced flow in order to occupy the void spaces within the web. Surface area per void volume (SA/VV) indicates how closely together those fiber surfaces are located to each other. Thus, the SA/VV value can be an important factor with respect to the amount of permeability for a structure. A high SA/VV value indicates there is a large amount of surface area which is placed closely together. Increases in SA/VV can be achieved by using smaller fibers which increase the surface area per unit weight of web, or by making the structure more dense which decreases the void volume per unit weight. When SA/VV is increased, permeability decreases since fluid is forced to travel over and around more surfaces to get through the structure. If the SA/VV becomes too high, then the permeability will be too low to allow easy fluid entry into and flow through the surge structure. Thus, SA/VV should be below 25 $cm^2$/cc in order for the permeability to be above about 8,000 darcy.

To ensure rapid intake of liquid, the overall structure should have hydrophilic tendencies. At least a portion of the fibers should have a contact angle less than 90 degrees. As a result, the fibrous nonwoven web will have sufficient hydrophilic tendencies when the web has a saturation capacity greater than 55 grams of 0.9% saline solution per gram of web.

Another important feature of the surge material employed with the present invention is its resiliency in both the wet and dry states. A unique feature of the surge material is the amount of liquid which the material is able to absorb upon rapid insult. In addition, once the liquid has been absorbed, the surge material does not readily collapse. Excessive collapse would be detrimental to the overall performance of the material in that the collapsing of the material would result in a reduced capacity for retaining liquid. Surge materials employed with the present invention should have compression resilience values in both the wet and dry states of at least about 60%.

Additional details regarding surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (Attorney docket No. 11,256); and in U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387). The disclosures of these documents are incorporated herein by reference to the extent that they are consistent herewith. The distinctive permeability, specific volume, porosity, and ratio of surface area to void volume parameters within the surge management portion of the invention can advantageously provide for a sufficiently rapid uptake of the liquid surges delivered onto the target zone, and also allow a controlled spreading of the liquid through the void volume of its structure to temporarily fill it. Over a relatively short period of time, the surge management portion can then be desorbed through the cooperative operation of the underlying or otherwise adjacent liquid retention portion.

The surge management portion is configured to cooperate with the other diaper components, such as top sheet 28 and retention portion 48, to provide for a rapid uptake of liquid discharges from the wearer. It is appreciated that a surge material with relatively small pore sizes may exhibit a rate of liquid penetration into the retention portion which may be too slow. A layer of surge management material having relatively large pore sizes, however, may provide insufficient restriction to sideways movement of liquid through the material along the plane of the material layer. As a result, the liquid may run off to the sides of the layer and leak from the article before the absorbent retention material can gather and contain the liquid. Such undesired, excessive run off may become more apparent when the absorbent material has already absorbed one or more previous discharges of liquid.

To help reduce the occurrence of excessive run off, the surge management portion present invention can be configured to have edge barriers constructed along selected edge regions thereof. In particular aspects, the edge barriers can be provided for by edge regions which are configured to include relatively small pores therein. The small pore regions can be located along the end edge regions and/or side edge regions of the surge management portion, and are configured to be sufficiently continuous to provide operable barriers to the sideways movement of liquid. The regions of small pores can, for example, be provided by employing a hot nip between a pair of heated rolls to melt a barrier seam at selected edge regions of the surge management portion. The hot nip can partially melt and densify the selected edge regions to reduce the pore size of the surge material and thereby inhibit the sideways flow of liquid.

Alternatively, a hot cutting mechanism may be employed to melt the selected edge regions of the surge material, and create a film-like edge at the selected regions. The cutting mechanism may, for example, be a hot knife, a hot cutting wire, or the like.

Optionally, the selected edge regions of the surge management portion may be treated with a sealant material, such as a latex sealant, silicone sealant or the like, to provide an operable barrier to the sideways flow of liquid. The sealant may be a hydrophobic material which inhibits the liquid flow by reducing the wettability of the surge material. The sealant may alternatively be a hydrophilic material which fills the pores of the surge material to thereby reduce or block the flow of liquid.

In other aspects, the edge barriers of the surge management portion can be provided for by a layer of liquid-resistent material wrapped around the selected edge regions of the surge material in a generally "c" configuration. Alternatively, the liquid resistent layer may be overlapped onto the bodyside surface of the surge material and extend in an operable engagement onto an underlying component, such as absorbent body 32 or backsheet 30, in a generally "z" configuration. The edge barrier material may, for example, be provided by a liquid impermeable polymer film, a fabric layer treated to render the fabric capable of supporting a substantial hydrohead substantially without leakage, or the like, or combinations thereof.

In the various configurations of the invention, the edge barrier may be provided at only the end edges 88 of the surge material. Alternatively, the edge barrier may be provided at only the side edges 84 and 86 of the surge material, and optionally may be provided at both the end and side edges of the surge material to provide desire performance.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article having elasticized side margins thereof, said article comprising:

a backsheet layer;

an absorbent retention portion which is superposed on said backsheet layer, said retention portion having a length and a width and having laterally opposed side edges thereof and longitudinally opposed end edges thereof;

a surge management portion located generally adjacent a bodyside surface of said retention portion, said surge management portion constructed to temporarily hold received liquid and release said liquid to said retention portion, said surge management portion having a width, opposed side edges thereof and opposed end edges thereof, and having a length thereof which is less than the length of said retention portion, said end edges of said surge management portion located longitudinally inboard from said end edges of said retention portion;

a porous topsheet layer which is disposed in facing relation with said backsheet layer to sandwich said retention portion and said surge management portion between said backsheet layer and said topsheet layer, said topsheet layer having marginal regions thereof attached to marginal regions of said backsheet layer, said marginal regions of said topsheet located outboard of a medial section of said topsheet, and said attached marginal regions of said topsheet and backsheet layers located laterally outboard of side edge regions of said surge management portion;

a surfactant material applied to said medial section of said topsheet layer to provide a greater wettability of said medial section, as compared to a remainder of said topsheet layer, said surfactant material applied to said medial section across a width which is substantially not more than said width of said surge management portion; and at least a pair of barrier flaps which are constructed of a spunbond-meltblown-spunbond laminate and are connected to laterally opposed, longitudinally extending regions of said topsheet layer, said regions located laterally inboard of said elasticized side margins and located substantially adjacent laterally opposed side regions of said topsheet medial section, each of said barrier flaps having a laterally extending base section thereof with at least a portion of said base section attached to said topsheet layer at a topsheet seam section and at a topsheet securement section, said securement section located laterally outboard of said retention portion and said surge management portion, said seam section located inboard of said securement section, said topsheet layer operably sealed to said barrier flaps and said backsheet layer at said securement section with a strip of adhesive having a width within a range of about 1–7 mm to substantially block a leakage of liquid through said securement section.

2. An absorbent article as recited in claim 1, wherein said attached marginal regions of said topsheet and backsheet layers are also located longitudinally outboard of end edge regions of said surge management portion.

3. An absorbent article as recited in claim 2, wherein said topsheet layer is constructed of a substantially hydrophobic material.

4. An absorbent article as recited in claim 3, wherein said topsheet layer includes a nonwoven fabric constructed of said substantially hydrophobic material.

5. An absorbent article as recited in claim 4, wherein said length of said surge management portion is not more than about 85% of said length of said retention portion.

6. An absorbent article as recited in claim 1, wherein said surge management portion includes edge barriers which are connected to said surge management portion along selected edge regions of said surge management portion.

7. An absorbent article as recited in claim 6, wherein said surge management portion includes pores therein and includes edge barriers which are constructed and connected to said surge management portion at selected edge regions thereof, and wherein said edge regions are configured with relatively small pores of reduced pore size therein to provide said edge barriers.

8. An absorbent article as recited in claim 6, wherein said edge regions of said surge management portion are treated with a sealant material to provide said edge barriers.

9. An absorbent article as recited in claim 6, wherein said edge regions of said surge management portion include another layer of liquid resistant material wrapped around said edge regions of said surge management portion in a generally "c" configuration to provide said edge barriers.

10. An absorbent article as recited in claim 1, wherein said surge management portion includes edge barriers which are constructed and connected to said surge management portion at selected side edge regions thereof.

11. An absorbent article as recited in claim 1, wherein said connected, longitudinally extending regions of said topsheet layer are located laterally outboard of said topsheet medial section.

12. An absorbent article as recited in claim 11, wherein said barrier flaps are constructed of a material which is permeable to gas.

13. An absorbent article as recited in claim 12, wherein said barrier flaps are constructed of a material which is resistant to a passage of liquid therethrough.

14. An absorbent article, comprising:
a backsheet layer;
an absorbent retention portion which is superposed on said backsheet layer, said retention portion having a length and a width and having laterally opposed side edges thereof and longitudinally opposed end edges thereof;
a surge management portion located generally adjacent a bodyside surface of said retention portion, said surge management portion constructed to temporarily hold received liquid and release said liquid to said retention portion, said surge management portion having a width, opposed side edges thereof and opposed end edges thereof, and having a length thereof which is less than the length of said retention portion, said end edges of said surge management portion located longitudinally inboard from said end edges of said retention portion; and
a porous topsheet layer which is disposed in facing relation with said backsheet layer to sandwich said retention portion and said surge management portion between said backsheet layer and said topsheet layer, said topsheet layer having marginal regions thereof attached to marginal regions of said backsheet layer, said attached marginal regions of said topsheet and backsheet layers located laterally outboard of side edge regions of said surge management portion;
said surge management portion comprising a fibrous nonwoven web having a basis weight of at least 20 grams per square meter, said web having a void volume of between about 80 and about 117 cubic centimeters per gram of web at 689 dynes per square centimeter pressure, a permeability of about 8,000 to about 15,000 darcy, a porosity of about 98.6 to about 99.4 percent, a surface area per void volume of about 10 to about 25 square centimeters per cubic centimeter.

15. An absorbent article as recited in claim 14, wherein said surge management portion has a basis weight within a range of about 40 to about 68 grams per square meter, and includes at least 50 percent by weight of bicomponent fibers.

16. An absorbent article as recited in claim 15, further comprising a surfactant material applied to a medial section of said topsheet layer to provide a greater wettability of said medial section, as compared to a remainder of said topsheet layer, said medial section having a width which is substantially not more than said width of said surge management portion.

17. An absorbent article comprising:
a backsheet layer;
an absorbent retention portion which is superposed on said backsheet layer, said retention portion having a length and a width and having laterally opposed side edges thereof and longitudinally opposed end edges thereof;
a surge management portion located generally adjacent a bodyside surface of said retention portion, said surge management portion constructed to temporarily hold received liquid and release said liquid to said retention portion, said surge management portion having a width, opposed side edges thereof and opposed end edges thereof, and having a length thereof which is less than the length of said retention portion, said end edges of said surge management portion located longitudinally inboard from said end edges of said retention portion, and said surge management portion comprising a bonded, substantially uniformly mixed, single layer structure having a basis weight of at least 20 grams per square meter, a void volume between about 40 and 60 cubic centimeters per gram of web at a pressure of 689 dynes per square meter, a permeability of about 5,000 to about 8,000 darcy, a porosity of about 97.2% to about 98.8% and a surface area per void volume of about 24 to about 49 square centimeters per cubic centimeters;
a porous topsheet layer which is disposed in facing relation with said backsheet layer to sandwich said retention portion and said surge management portion between said backsheet layer and said topsheet layer, said topsheet layer having marginal regions thereof attached to marginal regions of said backsheet layer, said marginal regions of said topsheet located outboard of a medial section of said topsheet, and said attached marginal regions of said topsheet and backsheet layers located laterally outboard of side edge regions of said surge management portion; and
a surfactant material applied to said medial section of said topsheet layer to provide a greater wettability of said medial section, as compared to a remainder of said topsheet layer, said surfactant material applied to said medial section across a width which is substantially not more than said width of said surge management portion.

18. An absorbent article as recited in claim 17, wherein said surge management portion has a density within a range of about 0.017–0.025 gm/cc.

19. An absorbent article, comprising:
a backsheet layer;
an absorbent retention portion which is superposed on said backsheet layer, said retention portion having a length and a width and having laterally opposed side edges thereof and longitudinally opposed end edges thereof;
a surge management portion located generally adjacent a bodyside surface of said retention portion, said surge management portion constructed to temporarily hold received liquid and release said liquid to said retention portion, said surge management portion having a width, opposed side edges thereof and opposed end edges thereof, and having a length thereof which is less than the length of said retention portion, said end edges of said surge management portion located longitudinally inboard from said end edges of said retention portion, and said surge management portion comprising a bonded, substantially uniformly mixed, single layer structure having a basis weight of at least 20 grams per square meter, a void volume between about 40 and 60 cubic centimeters per gram of web at a pressure of 689 dynes per square meter, a permeability of about 5,000 to about 8,000 darcy, a porosity of about 97.2% to about 98.8% and a surface area per void volume of about 24 to about 49 square centimeters per cubic centimeters;

a porous topsheet layer which is disposed in facing relation with said backsheet layer to sandwich said retention portion and said surge management portion between said backsheet layer and said topsheet layer, said topsheet layer having marginal regions thereof attached to marginal regions of said backsheet layer, said marginal regions of said topsheet located outboard of a medial section of said topsheet, and said attached marginal regions of said topsheet and backsheet layers located laterally outboard of side edge regions of said surge management portion;

an elastic member connected to each side margin of said backsheet layer to provide a pair of elasticized side margins of said article;

a pair of barrier flaps connected to laterally opposed, longitudinally extending regions of said topsheet layer, said regions located laterally inboard of said elasticized side margins and located substantially adjacent laterally opposed side regions of said topsheet medial section, each of said pair of barrier flaps having a laterally extending base section thereof with at least a portion of said base section attached to said topsheet layer at a topsheet seam section and at a topsheet securement section, said securement section located laterally outboard of said retention portion and surge management portion, said seam section located inboard of said securement section, and said topsheet layer operably sealed to said backsheet layer and to said barrier flaps at said securement section to substantially block a leakage of liquid through said securement section; and a surfactant material applied to said medial section of said topsheet layer to provide a greater wettability of said medial section, as compared to a remainder of said topsheet layer, said medial section with said applied surfactant having a width which is not more than a lateral spacing between said securement sections of said topsheet layer.

20. An absorbent article as recited in claim 19, wherein said surge management portion has a density within a range of about 0.017–0.025 gm/cc.

21. An absorbent article, comprising:

a backsheet layer;

an absorbent retention portion which is superposed on said backsheet layer, said retention portion having a length and a width and having laterally opposed side edges thereof and longitudinally opposed end edges thereof;

a surge management portion located generally adjacent a bodyside surface of said retention portion, said surge management portion constructed to temporarily hold received liquid and release said liquid to said retention portion, said surge management portion having a width, opposed side edges thereof and opposed end edges thereof, and having a length thereof which is less than the length of said retention portion, said end edges of said surge management portion located longitudinally inboard from said end edges of said retention portion;

a porous topsheet layer which is disposed in facing relation with said backsheet layer to sandwich said retention portion and said surge management portion between said backsheet layer and said topsheet layer, said topsheet layer having marginal regions thereof attached to marginal regions of said backsheet layer, said marginal regions of said topsheet located outboard of a medial section of said topsheet, and said attached marginal regions of said topsheet and backsheet layers located laterally outboard of side edge regions of said surge management portion;

an elastic member connected to each side margin of said backsheet layer to provide a pair of elasticized side margins of said article;

a pair of barrier flaps connected to laterally opposed, longitudinally extending regions of said topsheet layer, said regions located laterally inboard of said elasticized side margins and located substantially adjacent laterally opposed side regions of said topsheet medial section, each of said pair of barrier flaps having a laterally extending base section thereof with at least a portion of said base section attached to said topsheet layer at a topsheet seam section and at a topsheet securement section, said securement section located laterally outboard of said retention portion and surge management portion, said seam section located inboard of said securement section, and said topsheet layer operably sealed to said backsheet layer and to said barrier flaps at said securement section to substantially block a leakage of liquid through said securement section, and said topsheet securement section located laterally outboard from a corresponding side edge of said topsheet medial section; and a surfactant material applied to said medial section of said topsheet layer to provide a greater wettability of said medial section, as compared to a remainder of said topsheet layer, said medial section with said applied surfactant having a width which is not more than a lateral spacing between said securement sections of said topsheet layer.

22. An article as recited in claim 21, wherein said surfactant is applied to said medial section across a width which is not more than said width of said surge management portion.

23. An article as recited in claim 21, wherein said surge management portion comprises a bonded, substantially uniformly mixed, single layer structure having a basis weight of at least 20 grams per square meter, a void volume between about 40 and 60 cubic centimeters per gram of web at a pressure of 689 dynes per square meter, a permeability of about 5,000 to about 8,000 darcy, a porosity of about 97.2% to about 98.8% and a surface area per void volume of about 24 to about 49 square centimeters per cubic centimeter.

* * * * *